(12) United States Patent
Kanetani et al.

(10) Patent No.: US 8,742,149 B2
(45) Date of Patent: Jun. 3, 2014

(54) METALWORKING FLUID BASE OIL

(75) Inventors: Akinori Kanetani, Chiba (JP); Minako Matoba, Ichikawa (JP); Hiroyuki Izumoto, Tokyo (JP); Takaaki Kano, Tokyo (JP); Shingo Uemura, Tokyo (JP)

(73) Assignee: LION Corporation, Sumida-ku, Tokyo (JP)

( * ) Notice: Subject to any disclaimer, the term of this patent is extended or adjusted under 35 U.S.C. 154(b) by 0 days.

(21) Appl. No.: 13/809,547

(22) PCT Filed: Jul. 12, 2011

(86) PCT No.: PCT/JP2011/065873
§ 371 (c)(1),
(2), (4) Date: Jan. 10, 2013

(87) PCT Pub. No.: WO2012/008442
PCT Pub. Date: Jan. 19, 2012

(65) Prior Publication Data
US 2013/0116460 A1      May 9, 2013

(30) Foreign Application Priority Data
Jul. 12, 2010   (JP) ................. 2010-158075

(51) Int. Cl.
| C07C 59/00 | (2006.01) |
| B24C 3/08 | (2006.01) |
| B26D 1/00 | (2006.01) |

(52) U.S. Cl.
USPC ....................................................... 554/213

(58) Field of Classification Search
USPC .................................. 554/213; 451/28; 83/13
See application file for complete search history.

(56) References Cited

FOREIGN PATENT DOCUMENTS

| CN | 1548505 A1 | 11/2004 |
| CN | 101016498 A | 8/2007 |
| JP | 3-79697 | * 4/1991 |
| JP | A-03-079697 | 4/1991 |
| JP | 5-117683 | * 5/1993 |
| JP | A-05-117683 | 5/1993 |
| JP | A-07-316573 | 12/1995 |
| JP | A-08-169861 | 7/1996 |
| JP | 8-302381 | * 11/1996 |
| JP | A-08-302381 | 11/1996 |
| JP | 10-72589 | * 3/1998 |
| JP | A-10-072589 | 3/1998 |
| JP | A-2008-163115 | 7/2008 |
| JP | A-2009-275137 | 11/2009 |
| JP | A-2011-132470 | 7/2011 |
| WO | WO 99/64386 | * 12/1999 |
| WO | WO 99/64386 A1 | 12/1999 |

OTHER PUBLICATIONS

International Search Report for corresponding International Patent Application No. PCT/JP2011/065873 (mailed Oct. 25, 2011).
Chinese Office Action for corresponding Chinese Patent Application No. 201180038590.1 (mailed Oct. 23, 2013).

* cited by examiner

*Primary Examiner* — Deborah D Carr
(74) *Attorney, Agent, or Firm* — Merchant & Gould P.C.

(57) ABSTRACT

A water-insoluble cutting fluid base oil or grinding fluid base oil for metalworking includes a fatty acid polyoxyalkylene alkyl ether represented by the following formula (I-A), wherein a hydroxyl value of the fatty acid polyoxyalkylene alkyl ether is less than or equal to 2.0 mgKOH/g.

$$R^1\text{---CO-(OA)}_n\text{-OR}^3 \qquad \text{(I-A)}$$

(In the formula (I-A), $R^1$ represents a linear or branched, saturated or unsaturated monovalent hydrocarbon group having 15 to 21 carbon atoms and $R^3$ represents a linear, branched, or cyclic monovalent hydrocarbon group having 1 to 8 carbon atoms. In addition, A represents an alkylene group having 2 to 4 carbon atoms, OA represents alkylene oxide, and n represents 1 to 6 which is an average mole number of added alkylene oxide (AO)).

9 Claims, No Drawings

METALWORKING FLUID BASE OIL

This application is a U.S. National Stage Application under 35 U.S.C. §371 of International Patent Application No. PCT/JP2011/065873 filed 12 Jul. 2011, which claims the benefit of priority to Japanese Patent Application No. 2010-158075 filed 12 Jul. 2010, the disclosures of all of which are hereby incorporated by reference in their entireties. The International Application was published in Japanese on 19 Jan. 2012 as WO 2012/008442.

TECHNICAL FIELD

The present invention relates to a water-insoluble cutting fluid base oil and/or a water-insoluble grinding fluid base oil for metalworking which are used in metal cutting and grinding processes.

BACKGROUND

In metal cutting and grinding processes, in order to increase the lifetime of a tool and improve workability and productivity, a cutting fluid is generally used. Types of cutting fluid for metalworking include a water-soluble cutting fluid and a water-insoluble cutting fluid and the type to be used is determined according to a metal to be processed, process conditions, and required performance. For example, water-soluble cutting fluids are mainly used for dissipating heat generated during high-speed processing and reducing a risk of flammability but have a problem in that the content of base oil, such as mineral oil, included in the composition is small and the lubricity is poor. On the other hand, water-insoluble cutting fluids, the majority of which are composed of base oil, have excellent lubricity due to the action of the base oil, and therefore, are selected when lubricity is required for application to a material that is difficult to cut such as titanium, heat-resistant steel, ceramics, or aluminum alloy and accurate processing. However, commercially available water-insoluble cutting fluids are either fluids which belong to Class IV petroleums under the Japanese Fire Service Act and have a risk of combustion; or fluids which do not belong to Class IV petroleums under the Japanese Fire Service Act but have a high kinetic viscosity at 40° C. of 20 mm$^2$/s or higher and low cooling performance. Therefore, currently, there are no water-insoluble cutting fluids which satisfy the following three conditions: a low kinetic viscosity; high cooling performance; and a high flash point.

In order to obtain a water-insoluble cutting fluid base oil and a water-insoluble grinding fluid base oil which have a low kinetic viscosity and a high flash point, PTL 1 discloses a metalworking fluid composition obtained by mixing an oxygen-containing synthetic oil such as an ester, a mineral oil, and a hydrocarbon oil and adding an extreme pressure agent thereto, in which the kinetic viscosity at 40° C. is less than or equal to 37 mm$^2$/s and the flash point is higher than or equal to 250° C.

However, the kinetic viscosity at 40° C. of the metalworking fluid composition disclosed in PTL 1 is 37 mm$^2$/s, which is not suitable for practical use. For practical use, it is required that the kinetic viscosity at 40° C. be less than or equal to 14 mm$^2$/s. In addition, in PTL 1, a problem related to cooling performance is not solved. In addition, PTL 2 discloses a lubricant base oil in which there is less exhaust smoke and biodegradability and lubricity are improved. However, since the lubricant base oil disclosed in PTL 2 is used for a 2-cycle engine, it is clearly different from an object of the present invention as it is necessary that the lubricant base oil be burned along with fuel after lubrication. Furthermore, regarding the lubrication base oil for a 2-cycle engine, PTL 2 does not disclose the kinetic viscosity, surface tension, and hydroxyl value thereof.

In addition, PTL 3 discloses a base oil which is composed of one or two or more types of mineral oil, fat and oil, and synthetic esters, as one of the components constituting a hot rolling fluid composition. The invention disclosed in PTL 3 relates to a hot rolling fluid composition, which is clearly different from a water-insoluble cutting fluid base oil or grinding fluid base oil according to the present invention. Furthermore, PTL 3 discloses a kinetic viscosity of a mineral oil to be used but does not disclose a kinetic viscosity of an ester, and does not disclose the surface tension and flash point.

CITATION LIST

Patent Literature

[PTL 1] Japanese Unexamined Patent Application, First Publication No. 2008-163115
[PTL 2] Japanese Unexamined Patent Application, First Publication No. H7-316573
[PTL 3] Japanese Unexamined Patent Application, First Publication No. 2009-275137

SUMMARY

Technical Problem

It is strongly desirable to develop a water-insoluble cutting fluid base oil or grinding fluid base oil for metalworking which has a high flash point and excellent cooling performance whilst maintaining the kinetic viscosity thereof at a low level for excellent lubricating performance.

Solution to Problem

The present invention has been made in consideration of such circumstances.

In metalworking, heat is generated by the contact between a tool and a workpiece and cooling is performed by heat exchange of the tool, the workpiece and chips with metalworking fluid. In order to improve the cooling performance, it is considered that the following requirements are necessary: that a kinetic viscosity is low such that heat is easily diffused; and that fluid spreads out on small voids of metalworking points and the vicinity thereof rapidly and reliably (that is, an increase in the wettability of a base oil on a metal surface). Based on Young's equation expressing the relationship between the surface tension of a metal, the surface tension of a cutting fluid, and the contact angle of the cutting fluid and the metal, it is assumed that a low surface tension of a cutting fluid is important for wettability. As a result of a thorough study based on the above-described idea, the present inventors found that a component, which is a specific fatty acid polyoxyalkylene alkyl ether and has a structure in which a terminal is blocked with an alkyl group rather than an OH group, could solve the problems, thereby completing the present invention.

That is, the present invention adopts the following configurations in order to solve the problems.

[1] A water-insoluble cutting fluid base oil or grinding fluid base oil for metalworking including:
a fatty acid polyoxyalkylene alkyl ether represented by the following formula (I-A), wherein a hydroxyl value of the fatty acid polyoxyalkylene alkyl ether is less than or equal to 2.0 mgKOH/g.

[Chem. 1]

$$R^1\text{—CO-(OA)}_n\text{-OR}^3 \qquad (I\text{-}A)$$

(In the formula (I-A), $R^1$ represents a linear or branched, saturated or unsaturated monovalent hydrocarbon group having 15 to 21 carbon atoms and $R^3$ represents a linear, branched, or cyclic monovalent hydrocarbon group having 1 to 8 carbon atoms. In addition, A represents an alkylene group having 2 to 4 carbon atoms, OA represents alkylene oxide (hereinafter, referred to as "AO"), and n represents 1 to 6 which is an average mole number of added alkylene oxide.)

[2] The cutting fluid base oil or grinding fluid base oil for metalworking according to [1],
wherein the fatty acid polyoxyalkylene alkyl ether represented by the formula (I-A) is obtained by causing a compound (A) represented by the following formula (I) and a compound (B) represented by the following formula (II) to react with each other.

[Chem. 2]

$$R^1\text{—CO—OR}^2 \qquad (I)$$

[Chem. 3]

$$R^3\text{O-(AO)n-H} \qquad (II)$$

(In the formula (I), $R^2$ represents a monovalent hydrocarbon group having 1 to 18 carbon atoms and other reference numerals represent the same as above.)

[3] The cutting fluid base oil or grinding fluid base oil for metalworking according to [1] or [2],
wherein $R^1$ represents a monovalent hydrocarbon group having 17 carbon atoms.

[4] The cutting fluid base oil or grinding fluid base oil for metalworking according to [1] or [2],
wherein a fatty acid corresponding to a fatty acid unit ($R^1$CO unit) in the compound represented by the formula (I-A) or (I) is at least one type selected from the group consisting of an oleic acid, a C18 mixed fatty acid derived from palm, a C18 mixed fatty acid derived from soybean, a C18 mixed fatty acid derived from rapeseed, a C18 mixed fatty acid derived from rice bran, and a C18 mixed fatty acid derived from beef tallow.

[5] The cutting fluid base oil or grinding fluid base oil for metalworking according to [2],
wherein $R^2$ in the formula (I) represents a methyl group.

[6] The cutting fluid base oil or grinding fluid base oil for metalworking according to any one of [1] to [5],
wherein $R^3$ in the formula (I-A) or (II) represents at least one type selected from the group consisting of a methyl group, an isobutyl group, an n-butyl group, a t-butyl group and a 2-ethylhexyl group.

[7] The cutting fluid base oil or grinding fluid base oil for metalworking according to any one of [1] to [6],
wherein a kinetic viscosity at 40° C. is 7 to 14 mm²/s.

[8] The cutting fluid base oil or grinding fluid base oil for metalworking according to any one of [1] to [7],
wherein a surface tension is less than or equal to 34 mN/m.

[9] A method of cutting or grinding metal using a composition containing the fatty acid polyoxyalkylene alkyl ether represented by the formula (I-A) according to any one of [1] to [8].

Advantageous Effects of Invention

According to the present invention, by containing a fatty acid polyoxyalkylene alkyl ether represented by the formula (I-A), a water-insoluble cutting fluid base oil or grinding fluid base oil for metalworking having a low kinetic viscosity and excellent wettability on a metal surface can be obtained.

Therefore, cooling performance on a metal surface and metalworking points is excellent. Furthermore, since the flash point is high, the risk of combustion is reduced compared to the related art. In addition, since the kinetic viscosity is low, there is an advantage in that the amount of oil that becomes attached to a processed piece of metal and is discharged is reduced, which is economical.

Therefore, the present invention can be preferably applied to a rolling oil, a bearing oil, and the like, which requires a low kinetic viscosity and a high flash point, as well as a cutting fluid and a grinding fluid for metalworking.

DETAILED DESCRIPTION

A water-insoluble cutting fluid base oil or grinding fluid base oil for metalworking according to the present invention includes a fatty acid polyoxyalkylene alkyl ether represented by the following formula (I-A), in which a hydroxyl value of the fatty acid polyoxyalkylene alkyl ether is less than or equal to 2.0 mgKOH/g.

[Chem. 4]

$$R^1\text{—CO-(OA)}_n\text{-OR}^3 \qquad (I\text{-}A)$$

(In the formula (I-A), $R^1$ represents a linear or branched, saturated or unsaturated monovalent hydrocarbon group having 15 to 21 carbon atoms and $R^3$ represents a linear, branched, or cyclic monovalent hydrocarbon group having 1 to 8 carbon atoms. In addition, A represents an alkylene group having 2 to 4 carbon atoms and n represents 1 to 6 which is an average mole number of added alkylene oxide (AO).)

The hydroxyl value of the fatty acid polyoxyalkylene alkyl ether represented by the formula (I-A) is less than or equal to 2.0 mgKOH/g. Therefore, in a method of manufacturing the fatty acid polyoxyalkylene alkyl ether, it is more preferable that a process of causing a compound (A) represented by the following formula (I) and a compound (B) represented by the following formula (II) to react with each other and removing by-products and unreacted raw materials be performed. In addition, examples of a method of removing by-products and unreacted raw materials include a method of washing with water, a method using an adsorbent, a method using a filter aid, a method using pressure filtration, a method of distillation, and a method of distillation under reduced pressure. However, any of the examples can be used and a combination thereof can also be used.

[Chem. 5]

$$R^1\text{—CO—OR}^2 \qquad (I)$$

[Chem. 6]

$$R^3\text{O-(AO)n-H} \qquad (II)$$

(In the formula (I), $R^1$ represents a linear or branched, saturated or unsaturated monovalent hydrocarbon group having 15 to 21 carbon atoms and $R^2$ represents a monovalent hydrocarbon group having 1 to 18 carbon atoms. In the formula (3), $R^3$ represents a linear, branched, or cyclic monovalent hydrocarbon group having 1 to 8 carbon atoms, and A represents an alkylene group having 2 to 4 carbon atoms. In addition, n represents 1 to 6 which is an average mole number of added alkylene oxide.)

The hydrocarbon group represented by $R^1$ may be a saturated hydrocarbon group or an unsaturated hydrocarbon group. From the viewpoint that oxidation stability of the water-insoluble cutting fluid base oil or grinding fluid base oil for metalworking is excellent, it is preferable that an iodine value of the compound (A) represented by the formula (I) be less than or equal to 120. It is more preferable that the hydrocarbon group represented by $R^1$ be linear from the viewpoints of a high flash point and the availability of raw materials.

The number of carbon atoms of $R^1$ is 15 to 21. When the number of carbon atoms of $R^1$ is greater than or equal to 15, a high flash point is obtained. When the number of carbon atoms of $R^1$ is less than or equal to 21, an excessive increase in kinetic viscosity and surface tension can be prevented. In addition, it is more preferable that the number of carbon atoms of $R^1$ be 17 to 21 from the viewpoint of obtaining a high flash point, and it is still more preferable that the number of carbon atoms of $R^1$ be 15 to 17 from the viewpoint of obtaining a low kinetic viscosity and surface tension. It is particularly preferable that the number of carbon atoms be 17 from the viewpoint of obtaining highly satisfactory kinetic viscosity, surface tension, and flash point.

Specific examples of a fatty acid corresponding to a fatty acid unit ($R^1CO$ unit) in the compound (A) include palmitic acid, palmitoleic acid, stearic acid, isostearic acid, oleic acid, linoleic acid, linolenic acid, a C18 mixed fatty acid derived from palm (for example, a mixed fatty acid in which C 16:0/C18:0/C18:1/C18:2=3/10/70/17 (the ratio represents an area ratio using gas chromatography); the ratio of the mixed fatty acid can be determined with a general analysis method using gas chromatography; "X" of "C18:X" represents the number of unsaturated bonds), a C18 mixed fatty acid derived from rapeseed, a C16 to C18 mixed fatty acid derived from soybean, a C16 to C18 mixed fatty acid derived from palm kernel, a C18 mixed fatty acid derived from rice bran, a C18 mixed fatty acid derived from beef tallow, a mixed fatty acid derived from corn, a mixed fatty acid derived from safflower, arachidic acid, eicosadienoic acid, eicosatrienoic acid, arachidonic acid, behenic acid, and erucic acid. Among these, from the viewpoints of obtaining a base oil which satisfies a low kinetic viscosity, a low surface tension, and a high flash point and of obtaining a base oil having satisfactory fluidity at low temperature, an oleic acid, a C18 mixed fatty acid derived from palm, a C18 mixed fatty acid derived from soybean, a C18 mixed fatty acid derived from rapeseed, a C18 mixed fatty acid derived from rice bran, and a C18 mixed fatty acid derived from beef tallow are more preferable, and from the viewpoint of excellent oxidation stability, an oleic acid and a C18 mixed fatty acid derived from palm are particularly preferable.

$R^2$ represents a monovalent hydrocarbon group having 1 to 18 carbon atoms. Since $R^2$ is converted to alcohol by transesterification and removed, a carbon chain length is not particularly limited and a linear, branched, or cyclic hydrocarbon may be used. From the viewpoint of availability and reactivity of raw materials, a methyl group is preferable.

The hydrocarbon group represented by $R^3$ may be a saturated hydrocarbon group or an unsaturated hydrocarbon group, but a saturated hydrocarbon group is preferable from the viewpoint of excellent oxidation stability. The number of carbon atoms in $R^3$ is 1 to 8. When the number of carbon atoms in $R^3$ is less than or equal to 8, an excessive increase in kinetic viscosity and surface tension can be prevented while maintaining a high flash point.

When the number of carbon atoms in $R^3$ is 0, that is, when a terminal is an OH group, not only does the kinetic viscosity increase but the flash point decreases, which is not preferable. Whether or not there is an OH group at a terminal thereof is determined by analyzing a hydroxyl value of the compound. It is necessary that the water-insoluble cutting fluid base oil or grinding fluid base oil for metalworking according to the present invention contain a high-purity fatty acid polyoxyalkylene alkyl ether in which $R^3$ in the formula (I-A) represents a monovalent hydrocarbon group having 1 to 8 carbon atoms.

As an index indicating the purity of the fatty acid polyoxyalkylene alkyl ether represented by the formula (I-A), a hydroxyl value is used. "The hydroxyl value of the fatty acid polyoxyalkylene alkyl ether" or "the hydroxyl value in the fatty acid polyoxyalkylene alkyl ether" described in this specification represents that a hydroxyl value of unreacted materials of the formula (II) and/or a degradation product of the fatty acid polyoxyalkylene alkyl ether represented by the formula (I-A), which are produced during the preparation of the fatty acid polyoxyalkylene alkyl ether represented by the formula (I-A).

Specifically, a hydroxyl value in the fatty acid polyoxyalkylene alkyl ether according to the present invention is preferably less than or equal to 2.0 mgKOH/g, more preferably less than or equal to 1.0 mgKOH/g, and particularly preferably less than or equal to 0.6 mgKOH/g.

Specific examples of the hydrocarbon group represented by $R^3$ include a methyl group, an ethyl group, an isopropyl group, an n-propyl group, an isobutyl group, an n-butyl group, a tert-butyl group, a pentyl group, a hexyl group, a heptyl group, an octyl group, and a 2-ethylhexyl group. From the viewpoints of obtaining a low kinetic viscosity and surface tension, and a high flash point and furthermore of obtaining a base oil having excellent fluidity at low temperature, a methyl group, an isobutyl group, an n-butyl group, a tert-butyl group, and a 2-ethylhexyl group are more preferable. $R^3$ may represent one or more types among a methyl group, an ethyl group, an isopropyl group, an n-propyl group, an isobutyl group, an n-butyl group, a tert-butyl group, a pentyl group, a hexyl group, a heptyl group, an octyl group, a 2-ethylhexyl group, and the like, and preferably represents one type thereamong.

AO represents an oxyalkylene group formed by adding alkylene oxide having 2 to 4 carbon atoms, and examples thereof include an oxyethylene group, an oxypropylene group, and oxybutylene group. Among these, from the viewpoints of realizing a high flash point while maintaining a low kinetic viscosity and surface tension, an oxyethylene group and an oxypropylene group are more preferable. AO may be only one type of oxyalkylene group or may contain two or more types of oxyalkylene groups. When two or more types of the oxyalkylene groups are included, they may be added randomly or in a block shape.

An average mole number n of added AO is 1 to 6 and more preferably 2 to 5 from the viewpoint of simultaneously satisfying a low kinetic viscosity, a low surface tension, and a high flash point to a high degree. When n represents 1 or more, a high flash point can be realized while maintaining a low kinetic viscosity and surface tension. When n represents more than 6, kinetic viscosity and surface tension increases excessively, which is disadvantageous from the viewpoint of productivity.

A polyalkylene glycol alkyl ether of the compound (B) can be prepared by adding alkylene oxide (n=1 to 6) to alcohol having 1 to 8 carbon atoms. Furthermore, polyoxyalkylene alkyl ethers are commercially available in which a distribution of mole number added is narrowed by a purification treatment such as distillation or in which the mole number added is almost the same. By using these commercially available products as raw materials for esterification and transesterification of a fatty acid and a fatty acid alkyl ester, an alkylene oxide-added fatty acid ester having a narrow distribution of mole number of added AO, which is preferable in the present invention, can be easily obtained. Specific examples thereof include products manufactured by Nippon Nyukazai Co., Ltd. such as MFG (monopropylene glycol monomethyl ether), MFDG (dipropylene glycol monomethyl ether), MFTG (tripropylene glycol monomethyl ether), MG (monoethylene glycol monomethyl ether), MDG (diethylene glycol monomethyl ether), MTG (triethylene glycol monomethyl ether), MPG (polyethylene glycol monomethyl ether), BG (monoethylene glycol monobutyl ether), BDG (diethylene glycol monobutyl ether), BTG (triethylene glycol monobutyl ether), EHG (monoethylene glycol mono 2-ethylhexyl ether), and EHDG (diethylene glycol mono 2-ethylhexyl ether); and products manufactured by The Dow Chemical Company such as DOWANOL PM (monopropylene glycol monomethyl ether), DOWANOL DPM (dipropylene glycol monomethyl ether), DOWANOL TPM (tripropylene glycol monomethyl ether), and DOWANOL TPnB (tripropylene glycol monobutyl ether).

The above-described compound represented by the formula (I-A) according to the present invention can be prepared with a method of adding alkylene oxide to the corresponding monovalent alcohol and performing esterification of the obtained alkylene oxide adduct and a fatty acid, a method of performing transesterification of the obtained alkylene oxide adduct and a fatty acid alkyl ester, and a method disclosed in Japanese Unexamined Patent Application, First Publication No. H8-169861 of directly adding alkylene oxide to the corresponding fatty acid alkyl ester. Therefore, the mole number of added AO may have a distribution. It is preferable that this distribution of mole number added be narrower because physical properties, which are preferable from the viewpoints of both a low kinetic viscosity and a high flash point, are improved. As the distribution of mole number of added AO is wider, there is a concern that the flash point may decrease due to an increase in the content of a component having a lower molecular weight and a lower mole number added and that the kinetic viscosity and the surface tension may increase due to an increase in the content of a component having a high mole number added. Regarding the above-described compound represented by the formula (I-A) according to the present invention, one type or a mixture of two or more types may be included.

The water-insoluble cutting fluid base oil or grinding fluid base oil for metalworking according to the present invention may include other components in addition to the above-described compound represented by the formula (I-A) according to the present invention, within a range that secures the desired low kinetic viscosity, low surface tension, and high flash point.

Examples of other components include other base oils, for example, hydrocarbon oil such as mineral oil, poly-α-olefin, or isobutene; diester such as dioctyl sebacate (DOS), dioctyl adipate (DOA), neopentyl glycol dioleate; triester such as trimethylolpropane tricaprylate, trimethylolpropane trioleate, or medium-chain (having 6 to 12 carbon atoms) fatty acid triglyceride; polyol ester such as pentaerythritol tetracaprylate; complex ester; fatty acid alkyl ester; vegetable oil such as rapeseed oil, rice bran oil, soybean oil; silicon oil; fluoroether; phenylether; polyglycol; alkyl naphthalene; and phenyl xylyl ethane.

When the water-insoluble cutting fluid base oil or grinding fluid base oil for metalworking is represented by 100% by mass, a content of other components is preferably less than or equal to 50% by mass, more preferably less than or equal to 30% by mass, and particularly preferably less than or equal to 15% by mass, from the viewpoint of achieving a high flash point while maintaining a low kinetic viscosity and surface tension.

A kinetic viscosity at 40° C. of the water-insoluble cutting fluid base oil or grinding fluid base oil for metalworking according to the present invention is preferably 7 to 14 mm$^2$/s, more preferably 7 to 12 mm$^2$/s, and still more preferably 9 to 12 mm$^2$/s. When the kinetic viscosity at 40° C. is less than 7 mm$^2$/s, there is a concern that the flash point may decrease, an oil film may become thin and break, and lubricity may deteriorate, which is not preferable. When the kinetic viscosity at 40° C. is greater than 14 mm$^2$/s, the wettability and cooling performance on metalworking points are reduced. In addition, when the kinetic viscosity is high, the amount of oil that becomes attached onto processed metal chips and is discharged increases, which is not economical.

The kinetic viscosity at 40° C. represents a kinetic viscosity measured at 40° C. Even in a case where a kinetic viscosity measured at a temperature other than 40° C. is out of the range of 7 to 14 mm$^2$/s, if the kinetic viscosity is in the above-described range when converted into a kinetic viscosity at 40° C. and measured at 40° C., the kinetic viscosity is in the range according to the present invention.

The kinetic viscosity at 40° C. is measured in accordance with its K2283. For example, the kinetic viscosity at 40° C. is obtained by placing a sample into a Cannon-Fenske routine viscometer, leaving the sample to stand in a constant-temperature bath at 40° C. for 30 minutes or longer, and measuring a time when the sample is made to flow down from a given height in the Cannon-Fenske routine viscometer.

As a method of evaluating surface tension, various methods such as a capillary-rise method, a drop volume method, a ring method, a vertical plate method, a pendant drop method, and a maximum bubble pressure method are known. Any evaluation method can be used, but a vertical plate method is preferable from the viewpoint of performing evaluation with a relatively easy experimental procedure.

A surface tension of the water-insoluble cutting fluid base oil or grinding fluid base oil for metalworking according to the present invention is necessarily less than or equal to 34 mN/m from the viewpoints of the permeability to metalworking points and the formation of a lubricating film, and is preferably less than or equal to 33 mN/m, more preferably less than or equal to 32 mN/m, and particularly preferably less than or equal to 31 mN/m.

Since both of surface tension and kinetic viscosity are low, the wettability on metal is improved and heat is rapidly diffused. As a result, a rise in the temperature of oil, a tool, and a workpiece in a cutting field can be suppressed. By suppressing a rise in the temperature of oil, the oxidation of a cutting fluid is suppressed and the lifetime of a tool increases, which is useful.

A flash point of the water-insoluble cutting fluid base oil or grinding fluid base oil for metalworking according to the present invention is higher than or equal to 250° C. from the viewpoints of avoiding the risk of fire and the like and satisfying the legal requirements. When the flash point is lower than 250° C., the cutting fluid base oil or grinding fluid base oil is classified into Class IV hazardous materials under the Japanese Fire Service Act. On the other hand, when the flash point is higher than or equal to 250° C., the cutting fluid base oil or grinding fluid base oil is excluded from hazardous materials and is treated as a flammable liquid or designated combustible, which is preferable from the viewpoints of a reduction in the equipment required for treatment and the amount of stockpiling. In addition, since various additives are added to the cutting fluid base oil or grinding fluid base oil during the preparation, there is a possibility that the flash point may decrease. Therefore, it is more preferable that the flash point of the cutting fluid base oil or grinding fluid base oil is higher than or equal to 260° C.

The flash point is measured with a Cleveland open-cup flash point test in accordance with JIS K2265.

1) Preparation Method

The above-described alkylene oxide-added fatty acid ester represented by the formula (I-A) according to the present invention can be prepared with well-known methods of the related art according to the purpose and are not particularly limited, for example, a method of esterifying fatty acid with polyalkylene glycol alkyl ether (n=1 to 6), a method of performing transesterification of a fatty acid alkyl ester and polyalkylene glycol alkyl ether (n=1 to 6), a method of directly adding alkylene oxide to a fatty acid alkyl ester, a method of removing low-flash-point components by distillation or the like, and methods in accordance with the above-described methods and combinations of the above-described methods with usual methods.

No matter which method is used for obtaining a desired compound, a lower remaining amount of unreacted fatty acid alkyl ester as a raw material is preferable in order to obtain a high flash point. Specifically, the remaining amount is preferably less than or equal to 1%, more preferably less than or equal to 0.8%, and particularly preferably less than or equal to 0.5%. The remaining amount can be obtained with a general analysis method such as gas chromatography.

Similarly, in the compound represented by the formula (I-A) according to the present invention, that is, in the fatty acid polyoxyalkylene alkyl ether, it is important for a terminal to be blocked from the viewpoint of obtaining a high flash point and a low kinetic viscosity. As an index indicating a degree to which a terminal is blocked, a hydroxyl value is used. Specifically, the hydroxyl value is preferably less than or equal to 2.0 mgKOH/g, more preferably less than or equal to 1.0 mgKOH/g, and particularly preferably less than or equal to 0.6 mgKOH/g.

The base oil according to the present invention may have various additives added thereto as necessary, and is preferably used as a metalworking fluid, in particular, as a water-insoluble cutting fluid or grinding fluid.

2) Various Additives 2-1) Extreme Pressure Agent

It is preferable that the water-insoluble cutting fluid base oil or grinding fluid base oil for metalworking according to the present invention contain an extreme pressure agent from the viewpoints of improving process efficiency as a metalworking fluid and increasing the lifetime of a tool. Preferable examples of the extreme pressure agent include a sulfur compound and a phosphorus compound.

The sulfur compound is not particularly limited as long as it does not impair the characteristics of the metalworking fluid, and dihydrocarbyl polysulfide (for example, polysulfide or sulfurized olefin), sulfurized fatty acid (for example, sulfurized oleic acid), sulfurized olefin (obtained by causing olefin having 2 to 15 carbon atoms or a dimer to tetramer thereof to react with a sulfurizing agent such as sulfur or sulfur chloride), a sulfurized ester (examples thereof include animal or vegetable fat and oil such as beef tallow, lard, fish oil, rapeseed oil, or soybean oil; an unsaturated fatty acid ester obtained by causing an unsaturated fatty acid (including oleic acid, linoleic acid, and fatty acids extracted from the above-described animal or vegetable fat and oil) to react with various alcohols; and compounds obtained by sulfurizing a mixture thereof with a given method, and specific examples thereof include sulfurized methyl oleate, sulfurized rice bran fatty acid octyl, and a mixture thereof), sulfurized fat and oil (obtained by causing sulfur or a sulfur-containing compound to react with oil and fat (for example, lard oil, whale oil, vegetable oil, or fish oil) and examples thereof include sulfurized lard, sulfurized rapeseed oil, sulfurized castor oil, sulfurized soybean oil, and sulfurized rice bran oil), sulfurized mineral oil (obtained by dissolving sulfur in mineral oil; the mineral oil used for sulfurized mineral oil is not particularly limited), zinc dithiophosphate compounds, zinc dithiocarbamate compounds, molybdenum dithiophosphate compounds, molybdenum dithiocarbamate compounds, thiadiazole compounds (for example, 1,3,4-thiadiazole compounds, 1,2,4-thiadiazole compounds, and 1,4,5-thiadiazole compounds), alkylthiocarbamoyl compounds, thiocarbamate compounds, thioterpene compounds, and dialkyl thiodipropionate compounds are preferably used.

Specific examples of the phosphorus compound include phosphate ester, acid phosphate ester, acid phosphate ester amine salt, chlorinated phosphate ester, phosphite ester, phosphorothioate, and metal salt of phosphorus compounds. Examples of these phosphorus compounds include ester of phosphoric acid, phosphorous acid or thiophosphoric acid with alkanol or polyether type alcohol, and derivatives thereof.

More specifically, examples of the phosphate ester include tributyl phosphate, tripentyl phosphate, trihexyl phosphate, triheptyl phosphate, trioctyl phosphate, trinonyl phosphate, tridecyl phosphate, triundecyl phosphate, tridodecyl phosphate, tritridecyl phosphate, tritetradecyl phosphate, tripentadecyl phosphate, trihexadecyl phosphate, triheptadecyl phosphate, trioctadecyl phosphate, trioleyl phosphate, triphenyl phosphate, tricresyl phosphate, trixylenyl phosphate, cresyldiphenyl phosphate, and xylenyldiphenyl phosphate. Examples of the acid phosphate ester include monobutyl acid phosphate, monopentyl acid phosphate, monohexyl acid phosphate, monoheptyl acid phosphate, monooctyl acid phosphate, monononyl acid phosphate, monodecyl acid phosphate, monoundecyl acid phosphate, monododecyl acid phosphate, monotridecyl acid phosphate, monotetradecyl acid phosphate, monopentadecyl acid phosphate, monohexadecyl acid phosphate, monoheptadecyl acid phosphate, monooctadecyl acid phosphate, monooleyl acid phosphate, dibutyl acid phosphate, dipentyl acid phosphate, dihexyl acid phosphate, diheptyl acid phosphate, dioctyl acid phosphate, dinonyl acid phosphate, didecyl acid phosphate, diundecyl acid phosphate, didodecyl acid phosphate, ditridecyl acid phosphate, ditetradecyl acid phosphate, dipentadecyl acid phosphate, dihexadecyl acid phosphate, diheptadecyl acid phosphate, dioctadecyl acid phosphate, and dioleyl acid phosphate. Examples of the acid phosphate ester amine salt include salts of the above-described acid phosphate esters and amines such as methylamine, ethylamine, propylamine, butylamine, pentylamine, hexylamine, heptylamine, octylamine, dimethylamine, diethyl amine, dipropylamine, dibutylamine, dipentylamine, dihexylamine, diheptylamine, dioctylamine, trimethylamine, triethylamine, tripropylamine, tributylamine, tripentylamine, trihexylamine, triheptylamine, and trioctylamine. Examples of the chlorinated phosphate ester include trisdichloroprorylphosphate, trischloroethylphosphate, trischlorophenylphosphate, and polyoxyalkylenebis[di(chloroalkyl)]phosphate. Examples of the phosphite ester include dibutylphosphite, dipentylphosphite, dihexylphosphite, diheptylphosphite, dioctylphosphite, dinonylphosphite, didecylphosphite, diundecylphosphite, di dodecylphosph ite, dioleylphosphite, diphenylphosphite, dicresylphosphite, tributylphosphite, tripentylphosphite, trihexylphosphite, triheptylphosphite, trioctylphosphite, trinonylphosphite, tridecylphosphite, triundecylphosphite, tridodecylphosphite, trioleylphosphite, triphenylphosphite, and tricresylphosphite. Examples of the phosphorothionate include tributylphosphorothionate, tripentylphosphorothionate, trihexylphosphorothionate, triheptylphosphorothionate, trioctylphosphorothionate, trinonylphosphorothionate, tridecylphosphorothionate, triundecylphosphorothionate, tridodecylphosphorothionate, tritridecylphosphorothionate, tritetradecylphosphorothionate, tripentadecylphosphorothionate, trihexadecylphosphorothionate, triheptadecylphosphorothionate, trioctadecylphosphorothionate, trioleylphosphorothionate, triphenylphosphorothionate, tricresylphosphorothionate, trixylenylphosphorothionate, cresyldiphenylphosphorothionate, xylenyldiphenylphosphorothionate, tris(n-propylphenyl)phosphorothionate, tris(isopropylphenyl)phosphorothionate, tris(n-butylphenyl)phosphorothionate, tris(isobutylphenyl)phosphorothionate, tris(s-butylphenyl)phosphorothionate, and tris(t-butylphenyl) phosphorothionate.

Examples of the metal salt of phosphorus compounds include salts obtained by neutralizing, with a metal base, a part of or the whole acidic hydrogen of phosphorus compounds such as phosphorous acid, monothiophosphorous acid, phosphorous acid monoester, monothiophosphorous acid monoester, phosphorous acid diester, monothiophosphorous acid diester, phosphorous acid triester, monothiophosphorous acid trimester, phosphoric acid, monothiophosphoric acid, phosphoric acid monoester, monothiophosphoric acid monoester, phosphoric acid diester, monothiophosphoric acid diester, phosphoric acid triester, and monothiophosphoric acid triester. Examples of the metal base include metal oxide, metal hydroxide, metal carbonate, and metal chloride. Specific examples of the metal include alkali metals such as lithium, sodium, potassium, and cesium; alkaline earth metals such as calcium, magnesium, and barium; and heavy metals such as zinc, copper, iron, lead, nickel, silver, and manganese.

2-2) Oiliness Agent

It is preferable that the cutting fluid base oil or grinding fluid base oil according to the present invention contain an oiliness agent from the viewpoints of improving process efficiency as the metalworking fluid and increasing the lifetime of a tool. Examples of the oiliness agent include (a) alcohol, (b) carboxylic acid, (c) sulfide of unsaturated carboxylic acid, (d) p-tert-butylcatechol, (e) 2,2-dihydroxynaphthalene and 2,3-dihydroxynaphthalene, (f) polyoxyalkylene compound, (g) ester, (h) hydrocarbyl ether of polyol, and (i) amine.

According to the present invention, either the above-described extreme pressure agent or the above-described oiliness agent may be used or both of the extreme pressure agent and the oiliness agent may be used in combination from the viewpoints of preventing welding and process resistance from increasing and thus improving process efficiency and increasing the lifetime of a tool.

2-3) Organic Salt

In addition, it is preferable that the cutting fluid base oil or grinding fluid base oil according to the present invention as the metalworking fluid contain an organic salt from the viewpoints of improving process efficiency and increasing the lifetime of a tool. As the organic salt, sulfonate, phenate, salicylate, and a mixture thereof are preferably used. Examples of an cationic component of the organic salt include alkali metal such as sodium or potassium; alkaline earth metal such as magnesium, calcium, or barium; ammonia; amine such as alkyl amine with an alkyl group having 1 to 3 carbon atoms (for example, monomethylamine, dimethylamine, trimethylamine, monoethylamine, diethylamine, triethylamine, monopropylamine, dipropylamine, or tripropylamine) or alkanolamine with an alkanol group having 1 to 3 carbon atoms (monomethanolamine, dimethanolamine, trimethanolamine, monoethanolamine, diethanolamine, triethanolamine, monopropanolamine, dipropanolamine, or tripropanolamine); and zinc.

2-4) Antioxidant

In addition, it is preferable that the cutting fluid base oil or grinding fluid base oil according to the present invention as the metalworking fluid contain an antioxidant. By adding an antioxidant thereto, stickiness caused by changes of components can be prevented and furthermore heat and oxidation stability can be improved. Examples of the antioxidant to be used include phenolic antioxidant, aminic antioxidant, zinc dithiophosphate antioxidant, and other antioxidants which are used as a food additive.

2-5) Other Additives

In addition, the cutting fluid base oil or grinding fluid base oil according to the present invention as the metalworking fluid can contain well-known additives of the related art other than the above-described additives. Examples of the additives include an extreme pressure agent other than the above-described phosphorus compound and sulfur compound (including chlorine-based extreme pressure agent); a wetting agent such as diethylene glycol monoalkyl ether; a film-forming agent such as acryl polymer, paraffin wax, microcrystalline wax, slack wax, or polyolefin wax; a water-substituting agent such as fatty acid amine salt; a solid lubricant such as graphite, graphite fluoride, molybdenum disulfide, boron nitride, or polyethylene powder; a corrosion inhibitor such as amine, alkanolamine, amide, carboxylic acid, carboxylate, sulfonate, phosphoric acid, phosphate, or partial ester of polyol; metal deactivator such as benzotriazole or thiadiazole; an antifoaming agent such as methylsilicone, fluorosilicone, or polyacrylate; an ashless dispersant such as alkenyl succinimide, benzylamine, or polyalkenyl amine amino amide; a pour point depressant such as methacrylate-based polymer; a molecule-repairing agent; and an emulsifier.

3) Usage Method

In addition, the metalworking fluid using the water-insoluble cutting fluid base oil or grinding fluid base oil according to the present invention is excellent in process performance such as process speed, process efficiency, and surface roughness and furthermore in handleability and the lifetime of a tool. Therefore, the metalworking fluid is preferably used for a variety of applications of the metalworking field. The metalworking described herein is not limited to cutting and grinding processes and widely represents the entire field of metalworking. A method of supplying oil is not particularly limited, and a minimum quantity lubrication (MQL) method of spraying oil can be also used in addition to a normal supply method.

Specific examples of the metalworking include a cutting process, a grinding process, a form rolling process, a forging process, a press process, a drawing process, and a rolling process. Among these, the metalworking fluid based on the base oil according to the present invention is significantly efficient for a cutting process, grinding process, and the like.

In addition, the metalworking fluid based on the base oil according to the present invention has excellent process performance and thus is preferably used for a heavy process, a difficult process, or a process for materials that are difficult to process.

Furthermore, the metalworking fluid based on the water-insoluble cutting fluid base oil or grinding fluid base oil according to the present invention can be used as a lubricant oil for a portion other than processing sites of a machine tool, for example, oil for a sliding surface, oil for a bearing portion, or oil for a hydraulic machine. Therefore, the metalworking fluid is significantly efficient from the viewpoint of achieving space-saving and energy-saving of a machine tool.

The oil for a sliding surface described in the present invention represents a lubricant oil used for a guide mechanism, which guides sliding movement between two planes contacting each other, among components which are provided in a machine tool used for cutting and grinding processes. For example, in a machine tool in which a workpiece is disposed on a table, which is movable on a bed, and the table is moved to transport the workpiece toward tools for cutting and grinding processes, a sliding surface between the table and the bed is lubricated with the oil for a sliding surface. In addition, in a machine tool in which tools for cutting and grinding processes are fixed to a table, which is movable on a bed, and the table is moved to move the tools for cutting and grinding processes toward a workpiece, a sliding surface between the table and the bed is lubricated with the oil for a sliding surface.

In addition, a bearing portion is lubricated with lubrication methods such as oil bearing lubrication and mist bearing lubrication. The metalworking fluid based on the base oil according to the present invention can be applied to both methods.

The oil bearing lubrication represents a lubrication method of supplying a liquid lubricant oil to a bearing portion to promote smooth sliding in the bearing portion and the lubricant oil can also be expected to be used for cooling the bearing portion. Such a lubricant oil for oil bearing lubrication is required to be resistant to heat deterioration, that is, is required to have excellent heat resistance because the lubricant oil is used at a higher temperature portion. Nevertheless, the metalworking fluid based on the base oil according to the present invention can be used for the oil bearing lubrication.

The mist bearing lubrication represents a lubrication method in which a lubrication oil is converted to mist by a mist generator and the oil mist is supplied to a bearing portion along with a gas such as air to promote smooth sliding in the bearing portion. Since a cooling effect by air or the like can be expected at a high-temperature portion such as a bearing portion, there are many cases of adopting this lubrication method in recent machine tools. Such a lubricant oil for mist bearing lubrication is required to be resistant to heat deterioration, that is, is required to have excellent heat resistance because the lubricant oil is used at a higher temperature portion. Nevertheless, the metalworking fluid based on the base oil according to the present invention can be used for the mist bearing lubrication.

The hydraulic machine is operated and controlled by oil pressure, and in a hydraulic control portion in charge of the operation of devices, a hydraulic oil having lubrication, sealing, and cooling effects is used. Since the hydraulic oil operates devices by compressing a lubricant oil to a high pressure with a pump to generate oil pressure, the lubricant oil is required to have high lubricity, high oxidation stability, and heat stability. Nevertheless, the metalworking fluid based on the base oil according to the present invention can be used for the hydraulic oil.

EXAMPLES

Hereinafter, the present invention will be described in detail using Examples and Comparative Examples, but the present invention is not limited to the following Examples.

(1) Used Compound

Compounds (A), compounds (B), and compounds represented by the formula (I-A) according to the present invention obtained by a reaction, which were used in Examples and Comparative Examples, will be described below.

Compounds (A)

Fatty Acids or Fatty Acid Methyl Esters Used in Examples

A-1: methyl palmitate (manufactured by Lion Corporation, trade name "PASTELL M-16")

A-2: C18 mixed fatty acid methyl having methyl oleate as a main component (manufactured by Lion Corporation, trade name "PASTELL M-182")

A-3: oleic acid (manufactured by Natural Oleochemicals Sdn. Bhd., trade name: "Oleic acid, NOSB176/0169")

A-4: methyl stearate (manufactured by Lion Corporation, trade name: "PASTELL M-180")

A-5: methyl arachidonate (manufactured by Wako Pure Chemical Industries Ltd., reagent)

A-6: methyl behenate (manufactured by Wako Pure Chemical Industries Ltd., reagent)

Fatty Acids or Fatty Acid Methyl Esters Used in Comparative Examples

A'-7: methyl laurate (manufactured by Lion Corporation, trade name: "PASTELL M-12")

A'-8: lignoceric acid (manufactured by Wako Pure Chemical Industries Ltd., reagent)

Compounds (B)

Polyalkylene Glycol Alkyl Ethers Used in Examples

B-1: Tripropylene glycol monobutyl ether (manufactured by The Dow Chemical Company, trade name "DOWANOL TPnB")

B-2: triethylene glycol monomethyl ether (manufactured by Nippon Nyukazai Co., Ltd., trade name: "Methyltriglycol (MTG)")

B-3: polyethylene glycol monomethyl ether (manufactured by Nippon Nyukazai Co., Ltd., trade name: "Methylpolyglycol (MPG)")

B-4: triethylene glycol monobutyl ether (manufactured by Nippon Nyukazai Co., Ltd., trade name: "Butyltriglycol (BTG)")

B-5: diethylene glycol mono 2-ethylhexyl ether (manufactured by Nippon Nyukazai Co., Ltd., trade name: "2-ethylhexyldiglycol (EHDG)")

Polyalkylene Glycol Alkyl Ethers Used in Comparative Examples

B'-7: tripropylene glycol monomethyl ether (manufactured by Nippon Nyukazai Co., Ltd., trade name: "Methyl propylene triglycol (MFTG)")

B'-8: Polypropylene glycol monomethyl ether (intermediate prepared in Preparation Example 18)

Specific Examples of Compounds in Examples

I-1 Polyoxypropylene C18 mixed fatty acid butyl ether (M182-3P0-Bu, compound prepared in Preparation Example 1 described below)

I-2 Polyoxyethylene C18 mixed fatty acid methyl ether (M182-3EO-Me, compound prepared in Preparation Example 2 described below)

I-3 Polyoxyethylene stearic acid methyl ether (C18:0-4.2EO-Me, compound prepared in Preparation Example 3 described below)

I-4 Polyoxyethylene oleic acid methyl ether (C18:1-4.2EO-Me, compound prepared in Preparation Example 4 described below)

I-5 Polyoxyethylene C18 mixed fatty acid methyl ether (M182-4.2EO-Me, compound prepared in Preparation Example 5 described below)

I-6 Polyoxyethylene C18 mixed fatty acid butyl ether (M182-3EO-Bu, compound prepared in Preparation Example 6 described below)

I-7 Polyoxyethylene palmitic acid 2-ethylhexyl ether (C16:0-2EO-2EH, compound prepared in Preparation Example 7 described below)

I-8 Polyoxyethylene C18 mixed fatty acid 2-ethylhexyl ether (M182-2EO-2EH, compound prepared in Preparation Example 8 described below)

I-9 Polyoxyethylene arachidonic acid 2-ethylhexyl ether (C20:4-2EO-2EH, compound prepared in Preparation Example 9 described below)

I-10 Polyoxyethylene behenic acid 2-ethylhexyl ether (C22:0-2EO-2EH, compound prepared in Preparation Example 10 described below)

Compounds in Comparative Examples

I'-1 Polyoxyethylene lauric acid methyl ether (C12-3EO-Me, compound prepared in Preparation Example 11 described below)

I'-2 Polyoxypropylene lauric acid methyl ether (C12-3PO-Me, compound prepared in Preparation Example 12 described below)

I'-3 Polyoxypropylene lignoceric acid methyl ether (C24:0-3PO-Me, compound prepared in Preparation Example 13 described below)

Polyoxyethylene oleic acid (C18:1-2EO-OH, manufactured by Wako Pure Chemical Industries Ltd., polyoxyethylene monooleate, EO=2)

I'-5 Polyoxyethylene oleic acid (C18:1-6EO-OH, manufactured by Wako Pure Chemical Industries Ltd., polyoxyethylene monooleate, EO=6)

I'-6 Polyoxyethylene C18 mixed fatty acid 2-ethylhexyl ether (M182-2EO-2EH, compound prepared in Preparation Example 14 described below)

I'-7 Polyoxypropylene C18 mixed fatty acid methyl ether (M182-3PO-Me, compound prepared in Preparation Example 15 described below)

I'-8 Polyoxyethylene C18 mixed fatty acid alkyl ether (M182-3EO-secC12 to 14, compound prepared in Preparation Example 16 described below)

I'-9 Oleic acid 2-ethylhexyl (C18:1-2EH, manufactured by NOF Corporation, UNISTAR-MB-881)

I'-10 Polyoxyethylene C18 mixed fatty acid methyl ether (M182-7EO-Me, compound prepared in Preparation Example 17 described below)

I'-11 Polyoxypropylene C18 mixed fatty acid methyl ether (M182-7PO-Me, compound prepared in Preparation Example 18 described below)

(2) Evaluation Method

Regarding the cutting fluid base oil and grinding fluid base oil of the examples, measurement and evaluation methods for kinetic viscosity, surface tension, flash point, and the like will be shown below; and regarding cutting fluid performance, evaluation methods for the amount of oil discharged and cooling performance will be shown below.

[Kinetic Viscosity]

The kinetic viscosity (unit: $mm^2/s$) was measured in accordance with JIS K2283. A sample was placed into a Cannon-Fenske routine viscometer and left to stand in a constant-temperature bath at 40° C. for 30 minutes or longer. A time when the sample is made to flow down from a given height in the Cannon-Fenske routine viscometer was measured and a kinetic viscosity (unit: $mm^2/s$) at each temperature was calculated. The obtained kinetic viscosity values were classified into the following criteria and "A and AA" were considered to qualify.

<Evaluation Criteria>

AA: 12 $mm^2/s$ or less
A: greater than 12 $mm^2/s$ and 14 $mm^2/s$ or less
B: greater than 14 $mm^2/s$

[Surface Tension]

The surface tension was measured using a surface tensiometer (manufactured by Kyowa Interface Science Co., Ltd., KYOWA CBVP SURFACE TENSIOMETER A3). A clean glass plate was prepared, calibration was performed, and a sample was placed on a petri dish (diameter: 65 mm) to a depth of 8 mm. Then, when a liquid surface of the sample was in contact with the glass plate, a surface tension was read three times, and the average value thereof was recorded. A represents less than 34 mN/m and B represents 34 mN/m or greater, and "A" was considered to qualify.

[Flash Point]

The flash point was measured with a Cleveland open-cup flash point test in accordance with JIS K2265.

AA represents a flash point of 260° C. or higher, A represents a flash point of 250° C. or higher and lower than 260° C., and B represents a flash point of less than 250° C., and "A and AA" were considered to qualify.

[Evaluation for Amount of Oil Attached]

In accordance with JIS K2246 (rust prevent oils) 6.19, a test piece having a length of 80 mm, a width of 60 mm, and a thickness of 1 to 2 mm was dipped in a test oil for 1 minute and pulled out. The test piece was vertically suspended for 24 hours. The mass of the test piece was measured and converted to the amount of oil attached per unit area.

"A" represents an amount of oil attached of less than 5 $mg/cm^2$ and "B" represents an amount of oil attached of 5 $mg/cm^2$ or greater. "A" was considered to qualify.

[Cooling Performance]

A material defined by JIS A2017 was processed with an end mill for 10 minutes under the following conditions and a surface temperature (° C.) of a processed workpiece was measured to evaluate cooling performance.

When a surface temperature in the initial stage of process was 25±1° C., "A" represents a surface temperature of a processed metal surface of lower than 50° C. and "B" represents a surface temperature of 50° C. or higher. "A" was considered to qualify.

Used apparatus: vertical machining center MC-510VF (manufactured by Matsuura Machinery Corporation).
Workpiece: Its A2017 (aluminum alloy)
Tool material: high-speed toolsteel (JIS SKH4)
Cutting speed: V=200 m/min
Feed speed: f=0.1/rev
Cut depth: 3 mm
Initial temperature of oil: 25±1° C.
Amount of cutting fluid: 3 L/min

[Comprehensive Evaluation]

"A" in the comprehensive evaluation represents a case where all the evaluations for kinetic viscosity, flash point, and cooling performance were "A"; and "AA" in the comprehensive evaluation represents a case where the kinetic viscosity was "AA", the flash point was "A" or "AA", and the cooling performance was "A".

[Calculation Method of Average Mole Number Added]

Average mole numbers of added EO (ethylene oxide) and PO (propylene oxide) in the compound (B) were obtained by calculation from the mass balance of raw materials and alkylene oxide which were prepared. However, when distillation was performed after an addition reaction of EO and PO, the average mole number added was calculated according to $^1$H-NMR analysis described below.

30 mg of a compound was dissolved in 4 mL of deuterated chloroform and measurement was performed using $^1$H-NMR (300 MHz, manufactured by JEOL Ltd., FT NMR SYSTEM JNM-LA300). Using a chemical shift in deuterated chloroform of 7.30 ppm as a reference, the average mole number added was obtained by calculation from a ratio of integrated values of each peak of chemical shift at 0.87 ppm (terminal methyl derived from alcohol), 1.13 to 1.15 ppm (side chain methyl of PO), 3.32 to 3.66 ppm (methine and methylene of PO), and 3.52 to 3.71 ppm (methylene of EO).

[Quantitative Method of Terminal OH]

Regarding the obtained compound, a hydroxyl value of a sample was quantitatively measured in accordance with a phthalic anhydride method described in JIS K1557 "Testing method of polyether for polyurethane". In this test method, a compound having an OH group is caused to react with an excessive phthalic anhydride and a remaining amount of phthalic anhydride is titrated with N/2 sodium hydroxide solution to obtain the amount of the OH group.

30 g of a sample was weighed and put into a flask, and 25 ml of pyridine solution of phthalic anhydride was accurately added thereto with a whole pipette. An air condenser was mounted to the reaction flask and the reaction flask was heated in a constant-temperature bath at 98±2° C. for 2 hours while being occasionally shaken gently way. Then, the flask was left to stand until the temperature of the reaction mixture was cooled to room temperature. The air condenser was washed with pyridine and 50 ml of N/2 sodium hydroxide solution was accurately added with a whole pipette. Next, 5 droplets of pyridine solution of phenolphthalein were added as an indicator and further titrated with N/2 sodium hydroxide solution and a point where red color is maintained for at least 15 seconds was considered as the end point. A blank test was performed under the same condition. A hydroxyl value was calculated from the obtained results according to the following expression.

$$\text{Hydroxyl Value} = 28.05 \times (B-A) \times f/S$$

A: Amount (ml) of N/2 sodium hydroxide solution required to titrate sample
B: Amount (ml) of N/2 sodium hydroxide solution required to titrate blank
f: Factor of N/2 sodium hydroxide solution
S: Weight of sample (g)

PREPARATION METHOD OF COMPOUNDS IN EXAMPLES

Preparation Example 1

Preparation of I-1

1075 g of methyl oleate (C18 mixed fatty acid methyl ester having 18 carbon atoms derived from palm as main components (the number of carbon atoms in $R^1$—CO: C16/C18:0/C18:1/C18:2=3/10/70/17); trade name: PASTELL M-182, manufactured by Lion Corporation.), 944 g of tripropylene glycol monobutyl ether (manufactured by The Dow Chemical Company, trade name "DOWANOL TPnB"; 1.05 mole equivalents with respect to 1 mole of methyl oleate), and 2.0 g of tetraisopropoxy titanate (TPT) as a transesterification catalyst was put into a 5 four-necked flask, followed by nitrogen substitution. Then, while nitrogen was circulated at a flow rate of 1 mL/min, heating was performed until the liquid temperature was 160° C., followed by transesterification. Methanol produced by the reaction was removed by distillation. After methanol was removed, the temperature was raised to 280° C. while gradually reducing the pressure to 0.6 kPa. As a result, a crude product (F1) having a total amount of unreacted methyl oleate and tripropylene glycol monobutyl ether of 1% or lower was obtained. Next, 30 g (equivalent to 2% by mass with respect to the crude product (F1)) of KYOWAAD 500SH was added to 1500 g of the crude product (F1) and stirring was performed for 1 hour while maintaining the liquid temperature at 100° C., followed by absorptive treatment of a catalyst. Next, 7.5 g (equivalent to 0.5% by mass with respect to the crude product (F1)) of Hyflo Super-Cel as a filter aid was added, followed by stirring for 10 minutes and uniform dispersion. Then, pressure filtration was performed at 80° C. As a result, a compound I-1 (M182-3PO-Bu, $R^1=C_{17}H_{33}$, $R^3=C_4H_9$) having a hydroxyl value of 0.5 mgKOH/g was obtained.

Preparation Example 2

Preparation of I-2

A compound I-2 (M182-3EO-Me, $R^1=C_{17}H_{33}$, $R^3=CH_3$) having a hydroxyl value of 0.3 mgKOH/g was obtained with the same preparation method as that of Preparation Example 1, except that 739 g of triethylene glycol monomethyl ether (manufactured by Nippon Nyukazai Co., Ltd., trade name: "Methyltriglycol (MTG)") was used instead of tripropylene glycol monobutyl ether and 1273 g of C18 mixed fatty acid methyl ester derived from palm was used.

Preparation Example 3

Preparation of I-3

A compound I-3 (C18:0-4.2EO-Me, $R^1=C_{17}H_{35}$, $R^3=CH_3$) having a hydroxyl value of 0.8 mgKOH/g was obtained with the same preparation method as that of Preparation Example 1, except that 1139 g of methyl stearate (the number of carbon atoms in $R^1$—CO: C18:0; trade name: "PASTELL M-180", manufactured by Lion Corporation.) was used instead of the C18 mixed fatty acid methyl ester derived from palm and 868 g of polyethylene glycol monomethyl ether (manufactured by Nippon Nyukazai Co., Ltd., trade name: "Methylpolyglycol (MPG)") was used instead of tripropylene glycol monobutyl ether.

Preparation Example 4

Preparation of I-4

Instead of the C18 mixed fatty acid methyl ester derived from palm, 1091 g of oleic acid (the number of carbon atoms in $R^1$—CO: C18:1; manufactured by Natural Oleochemicals Sdn. Bhd., Oleic acid, NOSB176/0169), 890 g of polyethylene glycol monomethyl ether, and 4.95 g of PTS as an esterification catalyst were added thereto. Next, the temperature was raised to 180° C. under stirring. After water as a by-product was removed, the pressure was reduced to 0.6 kPa in a stepwise manner while raising the temperature to 210° C. Next, 30 g (equivalent to 2% by mass with respect to the crude product) of KYOWAAD 500SH was added to the obtained crude product and stirring was performed for 1 hour while maintaining the liquid temperature at 100° C., followed by absorptive treatment of the catalyst. Next, 7.5 g (equivalent to 0.5% by mass with respect to the crude product) of Hyflo SuperCel as a filter aid was further added, followed by stirring for 10 minutes and uniform dispersion. Then, pressure filtration was performed at 80° C. As a result, a compound I-4

(C18:1-4.2EO-Me, $R^1=C_{17}H_{33}$, $R^3=CH_3$) having a hydroxyl value of 1.3 mgKOH/g was obtained.

Preparation Example 5

Preparation of I-5

A compound I-5 (M182-4.2EO-Me, $R^1=C_{17}H_{33}$, $R^3=CH_3$) having a hydroxyl value of 0.5 mgKOH/g was obtained with the same preparation method as that of Preparation Example 1, except that 868 g of polyethylene glycol monomethyl ether was used instead of tripropylene glycol monobutyl ether and 1132 g of C18 mixed fatty acid methyl ester derived from palm was used.

Preparation Example 6

Preparation of I-6

A compound I-6 (M182-3EO-Bu, $R^1=C_{17}H_{33}$, $R^3=C_4H_9$) having a hydroxyl value of 0.7 mgKOH/g was obtained with the same preparation method as that of Preparation Example 1, except that 846 g of triethylene glycol monobutyl ether (manufactured by Nippon Nyukazai Co., Ltd., trade name: "Butyltriglycol (BTG)") was used instead of tripropylene glycol monobutyl ether and 1160 g of C18 mixed fatty acid methyl ester derived from palm was used.

Preparation Example 7

Preparation of I-7

A compound I-7 (C16:0-2EO-2EH, $R^1=C_{15}H_{31}$, $R^3=C_8H_{17}$) having a hydroxyl value of 0.1 mgKOH/g was obtained with the same preparation method as that of Preparation Example 1, except that 1080 g of methyl palmitate (the number of carbon atoms in $R^1$—CO: C16:0 methyl ester, trade name "PASTELL M-16", manufactured by Lion Corporation.) was used instead of the C18 mixed fatty acid methyl ester derived from palm and 917 g of diethylene glycol mono 2-ethylhexyl ether (manufactured by Nippon Nyukazai Co., Ltd., trade name: "2-ethylhexyldiglycol (EHDG)") was used instead of tripropylene glycol monobutyl ether.

Preparation Example 8

Preparation of I-8

A compound I-8 (M182-2EO-2EH, $R^1=C_{17}H_{33}$, $R^3=C_8H_{17}$) having a hydroxyl value of 0.3 mgKOH/g was obtained with the same preparation method as that of Preparation Example 1, except that 873 g of diethylene glycol mono 2-ethylhexyl ether was used instead of tripropylene glycol monobutyl ether and 1132 g of C18 mixed fatty acid methyl ester derived from palm was used.

Preparation Example 9

Preparation of I-9

A compound I-9 (C20:4-2EO-2EH, $R^1=C_{19}H_{31}$, $R^3=C_8H_{17}$) having a hydroxyl value of 0.9 mgKOH/g was obtained with the same preparation method as that of Preparation Example 1, except that 1183 g of arachidonic acid methyl ester (the number of carbon atoms in $R^1$—CO: C20:4 methyl ester, manufactured by Wako Pure Chemical Industries Ltd.) was used instead of the C18 mixed fatty acid methyl ester derived from palm and 851 g of diethylene glycol mono 2-ethylhexyl ether was used and the temperature was raised to 300° C.

Preparation Example 10

Preparation of I-10

A compound I-10 (C22:0-2EO-2EH, $R^1=C_{21}H_{43}$, $R^3=C_8H_{17}$) having a hydroxyl value of 1.8 mgKOH/g was obtained with the same preparation method as that of Preparation Example 1, except that 1215 g of behenic acid methyl ester (the number of carbon atoms in $R^1$—CO: C22:0 methyl ester, manufactured by Wako Pure Chemical Industries Ltd.) was used instead of the C18 mixed fatty acid methyl ester derived from palm and 786 g of diethylene glycol mono 2-ethylhexyl ether was used and the temperature was raised to 320° C.

Regarding the compounds obtained in Examples, the evaluation results for kinetic viscosity (40° C.), surface tension, flash point, and pour point and the evaluation results for amount of oil discharged and cooling performance are shown in Table 1.

TABLE 1

| | Example 1 I-1 | Example 2 I-2 | Example 3 I-3 | Example 4 I-4 | Example 5 I-5 | Example 6 I-6 | Example 7 I-7 | Example 8 I-8 | Example 9 I-9 | Example 10 I-10 |
|---|---|---|---|---|---|---|---|---|---|---|
| $R^1$—CO | M182 | M182 | C18:0 | C18:1 | M182 | M182 | C16:0 | M182 | C20:4 | C22:0 |
| $R^3$ | Bu | Me | Me | Me | Me | Bu | 2EH | 2EH | 2EH | 2EH |
| $R^2$ | Me | Me | Me | H | Me | Me | Me | Me | Me | Me |
| AO | PO | EO | EO | EO | EO | EO | EO | EO | EO | EO |
| n | 3 | 3 | 4.2 | 4.2 | 4.2 | 3 | 2 | 2 | 2 | 2 |
| Hydroxyl Value (mgKOH/g) | 0.5 | 0.3 | 0.8 | 1.3 | 0.5 | 0.7 | 0.1 | 0.3 | 0.9 | 1.8 |
| Kinetic Viscosity (mm²/s) | 11.9 | 9.6 | 12.3 | 12.1 | 12.0 | 10.9 | 10.4 | 11.5 | 12.6 | 13.9 |
| Evaluation | AA | AA | A | A | AA | AA | AA | AA | A | A |
| Surface Tension (mN/m) | 30.7 | 33.5 | 33.4 | 33.3 | 33.4 | 32.4 | 31.3 | 32.1 | 32.9 | 33.9 |
| Evaluation | A | A | A | A | A | A | A | A | A | A |
| Flash Point (° C.) | 254 | 251 | 269 | 255 | 267 | 254 | 250 | 260 | 268 | 272 |
| Evaluation | A | A | AA | A | AA | A | A | AA | AA | AA |

TABLE 1-continued

|  | Example 1 I-1 | Example 2 I-2 | Example 3 I-3 | Example 4 I-4 | Example 5 I-5 | Example 6 I-6 | Example 7 I-7 | Example 8 I-8 | Example 9 I-9 | Example 10 I-10 |
|---|---|---|---|---|---|---|---|---|---|---|
| Amount of Oil Discharged (mg/cm$^2$) | 4.4 | 4.2 | 4.5 | 4.5 | 4.4 | 4.3 | 4.3 | 4.4 | 4.5 | 4.7 |
| Evaluation | A | A | A | A | A | A | A | A | A | A |
| Temperature of Workpiece (° C.) | 42 | 40 | 44 | 44 | 44 | 41 | 40 | 43 | 46 | 48 |
| Evaluation for Cooling Performance | A | A | A | A | A | A | A | A | A | A |
| Comprehensive Evaluation | AA | AA | A | A | AA | AA | AA | AA | A | A |

Preparation Method of Compounds in Comparative Examples

Preparation Example 11

Preparation of I'-1

A compound I'-1 (C12-3EO-Me, $R^1$=$C_{11}H_{23}$, $R^3$=$CH_3$) having a hydroxyl value of 0.1 mgKOH/g was obtained with the same preparation method as that of Preparation Example 1, except that 1123 g of methyl laurate (the number of carbon atoms in $R^1$—CO: C12 methyl ester; trade name: "PASTELL M-12", manufactured by Lion Corporation.) was used instead of the C18 mixed fatty acid methyl ester derived from palm; 903 g of triethylene glycol monomethyl ether was used instead of tripropylene glycol monobutyl ether; and the temperature was raised to 230° C.

Preparation Example 12

Preparation of I'-2

A compound I'-2 (C12-3PO-Me, $R^1$=$C_{11}H_{23}$, $R^3$=$CH_3$) having a hydroxyl value of 0.3 mgKOH/g was obtained with the same preparation method as that of Preparation Example 1, except that 1032 g of tripropylene glycol monomethyl ether was used instead of tripropylene glycol monobutyl ether and 1021 g of methyl laurate was used and the temperature was raised to 230° C.

Preparation Example 13

Preparation of I'-3

A compound I'-3 (C24:0-3PO-Me, $R^1$=$C_{23}H_{47}$, $R^3$=$CH_3$) having a hydroxyl value of 0.9 mgKOH/g was obtained with the same preparation method as that of Preparation Example 4, except that 1228 g of lignoceric acid (the number of carbon atoms in $R^1$—CO: C24:0, manufactured by Wako Pure Chemical Industries Ltd.) was used instead of oleic acid and 722 g of tripropylene glycol monomethyl ether was used.

Preparation Example 14

Preparation of I'-6

A compound I'-6 (M182-2EO-2EH, $R^1$=$C_{17}H_{33}$, $R^3$=$C_8H_{17}$) having a hydroxyl value of 3.6 mgKOH/g was obtained with the same preparation method as that of Preparation Example 1, except that 873 g of diethylene glycol mono 2-ethylhexyl ether and 1132 g of C18 mixed fatty acid methyl ester derived from palm were used and the pressure was reduced to 1.2 kPa when the raw materials were removed after the methanol as a by-product was removed.

Preparation Example 15

Preparation of I'-7

A compound I'-7 (M182-3PO-Me, $R^1$=$C_{17}H_{33}$, $R^3$=$CH_3$) having a hydroxyl value of 2.5 mgKOH/g was obtained with the same preparation method as that of Preparation Example 14, except that 825 g of tripropylene glycol monomethyl ether (manufactured by Nippon Nyukazai Co., Ltd., trade name: "Methyl propylene triglycol (MFTG)") was used instead of diethylene glycol mono 2-ethylhexyl ether and 1132 g of C18 mixed fatty acid methyl ester derived from palm was used.

Preparation Example 16

Preparation of I'-8

A compound I'-8 (M182-3EO-C12 to 14, $R^1$=$C_{17}H_{33}$, $R^3$=$C_{12}H_{25}$ to $C_{14}H_{29}$) having a hydroxyl value of 1.0 mgKOH/g was obtained with the same preparation method as that of Preparation Example 1, except that 1102 g of SOFT-ANOL 30 (the number of $R^3$: 12 to 14; C12 to 14-3EO, manufactured by Nippon Shokubai Co., Ltd.) was used instead of tripropylene glycol monobutyl ether and 934 g of C18 mixed fatty acid methyl ester derived from palm was used.

Preparation Example 17

Preparation of I'-10

Nitrogen substitution was performed two times in a 4 autoclave and 1478 g of triethylene glycol monomethyl ether (manufactured by Nippon Nyukazai Co., Ltd., trade name: "Methyltriglycol (MTG)") and 8.9 g of 28% by mass sodium methoxide as a catalyst were put thereinto. Then, the temperature was raised to 90° C. and 991 g (equivalent to 2.5 mole with respect to 1 mole of MTG) of EO was gradually introduced to perform an EO addition reaction. When EO was introduced, the pressure was 0.48 MPa. The pressure was reduced along with the progress of the reaction. After 1 hour, the EO addition reaction was continued until the pressure was maintained at 0.29 MPa. After cooling was performed, 20 g (1% by mass with respect to the crude product) each of KYOWAAD 600S and KYOWAAD 700SL (both of which are inorganic synthetic adsorbents, manufactured by Kyowa Chemical Industry Co., Ltd.) was added and stirring was performed at 95° C. for 30 minutes, followed by absorptive treatment of the catalyst. A first intermediate A' (MeO-5.5EO-H) was obtained by performing pressure filtration at 80° C. for solid-liquid separation. Furthermore, the temperature was raised from ordinary temperature to 180° C. while reducing the pressure from ordinary pressure to 5 Torr (0.7 kPa) in a stepwise manner. As a result, a second intermediate A' (MeO-7EO-H, distilled product), in which a low-boiling-point fraction having a mole number of added EO of 0 to 4 was removed, was obtained.

Next, a compound I'-10 (M182-7EO-Me, $R^1=C_{17}H_{33}$, $R^3=CH_3$) having a hydroxyl value of 0.5 mgKOH/g was obtained with the same preparation method as that of Preparation Example 1, except that 1089 g of the second intermediate A' was used instead of tripropylene glycol monobutyl ether and 905 g of C18 mixed fatty acid methyl ester derived from palm was used.

Preparation Example 18

Preparation of I'-11

Nitrogen substitution was performed two times in a 4 autoclave and 388 g of methanol (manufactured by Junsei Chemical Co., Ltd.), and 8.9 g of 28% by mass sodium methoxide as a catalyst were put thereinto. Then, the temperature was raised to 90° C. and 2112 g (equivalent to 3.0 mole with respect to 1 mole of methanol) of PO was gradually introduced to perform a PO addition reaction. When PO was introduced, the pressure was 0.48 MPa. The pressure was reduced along with the progress of the reaction. After 2 hours, the PO addition reaction was continued until the pressure was maintained at 0.39 MPa. As a result, a first intermediate B' (MeO-3PO—H) was obtained. 1223 g of the first intermediate B' was put into a 4 autoclave. Then, the temperature was raised to 90° C. and 861 g (equivalent to 2.5 mole with respect to 1 mole of the first intermediate B') of PO was gradually introduced to perform a PO addition reaction. When PO was introduced, the pressure was 0.49 MPa. Then, the pressure was reduced along with the progress of the reaction. After 2 hours, the PO addition reaction was continued until the pressure was maintained at 0.38 MPa. After cooling was performed, 20 g (1% by mass with respect to the crude product) each of KYOWAAD 600S and KYOWAAD 700SL (both of which are inorganic synthetic adsorbents, manufactured by Kyowa Chemical Industry Co., Ltd.) was added and stirring was performed at 95° C. for 30 minutes, followed by absorptive treatment of the catalyst. A second intermediate B' (MeO-5.5PO—H) was obtained by performing pressure filtration at 80° C. for solid-liquid separation. Furthermore, the temperature was raised from ordinary temperature to 200° C. while reducing the pressure from ordinary pressure to 5 Torr (0.7 kPa) in a stepwise manner. As a result, a third intermediate B' (MeO-7PO—H, distilled product), in which a low-boiling-point fraction having a mole number of added PO of 0 to 4 was removed, was obtained.

A compound I'-11 (M182-7PO-Me $R^1=C_{17}H_{33}$, $R^3=CH_3$) having a hydroxyl value of 0.3 mgKOH/g was obtained with the same preparation method as that of Preparation Example 1, except that 1228 g of the third intermediate B' was used instead of tripropylene glycol monobutyl ether and 792 g of C18 mixed fatty acid methyl ester derived from palm was used.

In the compounds I'-4 and I'-5 in Comparative Examples, a reagent was used and in the compound I'-9, a commercially available product was used.

Regarding I'-4

Regarding I'-4 (C18:1-2EO-OH, $R^1=C_{17}H_{33}$, $R^3=H$) having a comparative structure in which a terminal is OH, the hydroxyl value was 152.4 mgKOH/g when measured with the same method as that of Preparation Example 1.

Regarding I'-5

Likewise, regarding I'-5 (C18:1-6EO-OH, $R^1=C_{17}H_{33}$, $R^3=H$) having a comparative structure in which a terminal is OH, the hydroxyl value was 103.1 mgKOH/g when measured with the same method as that of Preparation Example 1.

Regarding I'-9

Regarding I'-9 (C18:1-2EH, $R^1=C_{17}H_{33}$, $R^3=C_8H_{17}$) having a comparative structure which did not include an alkylene oxide structure, the hydroxyl value was 0.1 mgKOH/g when measured with the same method as that of Preparation Example 1.

Regarding the compounds obtained in Comparative Examples, the evaluation results for kinetic viscosity (40° C.), surface tension, flash point, and pour point and the evaluation results for amount of oil discharged and cooling performance are shown in Table 2.

TABLE 2

| | Comparative Example 1 I'-1 | Comparative Example 2 I'-2 | Comparative Example 3 I'-3 | Comparative Example 4 I'-4 | Comparative Example 5 I'-5 | Comparative Example 6 I'-6 | Comparative Example 7 I'-7 | Comparative Example 8 I'-8 | Comparative Example 9 I'-9 | Comparative Example 10 I'-10 | Comparative Example 11 I'-11 |
|---|---|---|---|---|---|---|---|---|---|---|---|
| $R^1$—CO | C12 | C12 | C24:0 | C18:1 | C18:1 | M182 | M182 | M182 | C18:1 | M182 | M182 |
| $R^3$ | Me | Me | Me | H | H | 2EH | Me | C12 to C14 | 2EH | Me | Me |
| $R^2$ | Me | Me | H | Me | Me | Me | Me | Me | H | Me | Me |
| AO | EO | PO | PO | EO | EO | EO | PO | EO | — | EO | PO |
| n | 3 | 3 | 3 | 2 | 6 | 2 | 3 | 3 | 0 | 7 | 7 |
| Hydroxyl Value (mgKOH/g) | 0.1 | 0.3 | 0.9 | 152.4 | 103.1 | 3.6 | 2.5 | 1 | 0.1 | 0.5 | 0.3 |
| Kinetic Viscosity (mm²/s) | 6.5 | 7.0 | 14.8 | 22.7 | 36.7 | 11.4 | 10.4 | 17.5 | 8.2 | 16.8 | 20.1 |
| Evaluation | AA | AA | B | B | B | AA | AA | B | AA | B | B |
| Surface Tension (mN/m) | 32.2 | 29.9 | 35.1 | 34.4 | 34.3 | 32.1 | 30.9 | 30.7 | 31.8 | 34.8 | 31.4 |
| Evaluation | A | A | B | B | B | A | A | A | A | B | A |

TABLE 2-continued

| | Comparative Example 1 I'-1 | Comparative Example 2 I'-2 | Comparative Example 3 I'-3 | Comparative Example 4 I'-4 | Comparative Example 5 I'-5 | Comparative Example 6 I'-6 | Comparative Example 7 I'-7 | Comparative Example 8 I'-8 | Comparative Example 9 I'-9 | Comparative Example 10 I'-10 | Comparative Example 11 I'-11 |
|---|---|---|---|---|---|---|---|---|---|---|---|
| Flash Point (° C.) | 204 | 200 | 272 | 172 | 236 | 243 | 245 | 258 | 224 | 268 | 264 |
| Evaluation | B | B | AA | B | B | B | B | A | B | AA | AA |
| Amount of Oil Discharged (mg/cm$^2$) | 3.9 | 3.9 | 4.8 | 5.6 | 7.1 | 4.4 | 4.3 | 5.0 | 4.0 | 5.0 | 5.3 |
| Evaluation | A | A | A | B | B | A | A | B | A | B | B |
| Temperature of Workpiece (° C.) | 38 | 37 | 49 | 55 | 60 | 43 | 41 | 51 | 39 | 52 | 54 |
| Evaluation for Cooling Performance | A | A | A | B | B | A | A | B | A | B | B |
| Comprehensive Evaluation | B | B | B | B | B | B | B | B | B | B | B |

As shown in Table 1, in Examples 1 to 10 to which the present invention was applied, a low kinetic viscosity at 40° C. of 13.9 mm$^2$/s or less was shown and a low surface tension of 33.9 mN/m or less was shown. In addition, in Examples 1 to 10, a flash point of 250° C. or higher was shown. In particular, in Examples 1, 2, 5, 6, 7, and 8, since a low kinetic viscosity of 12 mm$^2$/s was shown, both the evaluation for kinetic viscosity and the comprehensive evaluation were "AA".

On the other hand, as shown in Table 2, in Comparative Examples 1 and 2 having a small number of carbon atoms in R$^1$—CO of 12, the kinetic viscosity was "AA" and the surface tension was "A"; however the flash point at about 200° C. was B. In Comparative Example 3 having a large number of carbon atoms in R$^1$—CO of C24:0, the flash point was "AA"; however, the kinetic viscosity at 40° C. and the surface tension were "B". In Comparative Examples 4 and 5 in which the number of carbon atoms in R$^3$ was 0, that is, a terminal was an OH group, even though the molecular weight was less than that of Examples, high kinetic viscosity values at 40° C. of 22.7 mm$^2$/s and 36.7 mm$^2$/s were shown and thus the kinetic viscosity was "B". Furthermore, high surface tension values of 34.3 mN/m and 34.4 mN/m were shown and thus the surface tension was "B". In addition, the flash point of less than 250° C. was shown and thus the flash point was "B". Therefore, all the performances were inferior to the compound in Examples. In Comparative Example 6 in which the hydroxyl value was greater than or equal to 3.6 mgKOH/g, the flash point dropped despite the same structure as that of Example 8. Accordingly, the flash point was "B". In Comparative Example 8 in which the number of carbon atoms in R$^3$ was more than or equal to 12, the surface tension and the flash point were "A", but the kinetic viscosity at 40° C. was "B". In Comparative Example 9 not having an AO structure, the kinetic viscosity and the surface tension were "A", but the flash point was "B". In Comparative Examples 10 and 11 having a large mole number of added AO of 7, the flash point was "AA", but the kinetic viscosity and the surface tension were "B".

In addition, in Examples 1 to 10 having a low kinetic viscosity, the amount of oil discharged was 4.7 mg/cm$^2$ at a maximum and the amount of oil discharged was reduced by 6 to 34% as compared to Comparative Examples 4, 5, 8, 10, and 11 having a high kinetic viscosity. In all the Examples, the cooling performance on a metal surface was improved, as compared to Comparative Examples 4, 5, 8, 10, and 11. In Comparative Examples 1, 2, 3, 6, 7, and 9 in which the amount of oil discharged and the cooling performance were superior, the flash point was low and it was not possible to avoid the risk of combustion sufficiently, which was inadequate in practice.

It was determined from these results that, when the water-insoluble cutting fluid base oil or grinding fluid base oil for metalworking according to the present invention is used, a low kinetic viscosity and surface tension can be satisfied while maintaining a high flash point and thus the cooling performance on a metal surface and metalworking points is excellent and the risk of combustion can be reduced.

Industrial Applicability

The water-insoluble cutting fluid base oil or grinding fluid base oil for metalworking according to the present invention has a low kinetic viscosity, a high flash point, and a low surface tension and thus is preferably used for metal cutting and grinding processes.

We claim:

1. A water-insoluble cutting fluid base oil or grinding fluid base oil for metalworking comprising:
    a fatty acid polyoxyalkylene alkyl ether represented by the following formula (I-A),
    wherein a hydroxyl value of the fatty acid polyoxyalkylene alkyl ether is less than or equal to 2.0 mgKOH/g

[Chem. 1]

$$R^1\text{—CO-(OA)}_n\text{-OR}^3 \quad \text{(I-A)}$$

in the formula (I-A), R$^1$ represents a linear or branched, saturated or unsaturated monovalent hydrocarbon group having 15 to 21 carbon atoms and R$^3$ represents a linear, branched, or cyclic monovalent hydrocarbon group having 1 to 8 carbon atoms; in addition, A represents an alkylene group having 2 to 4 carbon atoms, OA represents alkylene oxide, and n represents 1 to 6 which is an average mole number of added alkylene oxide.

2. The cutting fluid base oil or grinding fluid base oil for metalworking according to claim 1,
    wherein the fatty acid polyoxyalkylene alkyl ether represented by the formula (I-A) is obtained by causing a compound (A) represented by the following formula (I) and a compound (B) represented by the following formula (II) to react with each other

[Chem. 2]

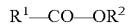
$$R^1-CO-OR^2 \quad (I)$$

[Chem. 3]

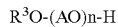
$$R^3O\text{-}(AO)n\text{-}H \quad (II)$$

wherein in the formula (I), $R^2$ represents a monovalent hydrocarbon group having 1 to 18 carbon atoms and other reference symbols represent the same as above.

3. The cutting fluid base oil or grinding fluid base oil for metalworking according to claim 1,
wherein $R^7$ represents a monovalent hydrocarbon group having 17 carbon atoms.

4. The cutting fluid base oil or grinding fluid base oil for metalworking according to claim 1,
wherein a fatty acid corresponding to a fatty acid unit ($R^1$CO unit) in the compound represented by the formula (I-A) or (I) is at least one type selected from the group consisting of an oleic acid, a C18 mixed fatty acid derived from palm, a C18 mixed fatty acid derived from soybean, a C18 mixed fatty acid derived from rapeseed, a C18 mixed fatty acid derived from rice bran, and a C18 mixed fatty acid derived from beef tallow.

5. The cutting fluid base oil or grinding fluid base oil for metalworking according to claim 2,
wherein $R^2$ in the formula (I) represents a methyl group.

6. The cutting fluid base oil or grinding fluid base oil for metalworking according to claim 1,
wherein $R^3$ in the formula (I-A) or (II) represents at least one type selected from the group consisting of a methyl group, an isobutyl group, an n-butyl group, a t-butyl group and a 2-ethylhexyl group.

7. The cutting fluid base oil or grinding fluid base oil for metalworking according to claim 1,
wherein a kinetic viscosity at 40° C. is 7 to 14 mm²/s.

8. The cutting fluid base oil or grinding fluid base oil for metalworking according to claim 1,
wherein a surface tension is less than or equal to 34 mN/m.

9. A method of cutting or grinding metal using a composition containing the fatty acid polyoxyalkylene alkyl ether represented by the formula (I-A) according to claim 1.

* * * * *